United States Patent
Zunker et al.

(10) Patent No.: US 6,645,136 B1
(45) Date of Patent: Nov. 11, 2003

(54) INCONTINENCE INSERT APPLICATORS AND METHODS FOR THEIR USE

(75) Inventors: MaryAnn Zunker, Oshkosh, WI (US); Herb F. Velazquez, Neenah, WI (US); Donald J. Sanders, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/675,458

(22) Filed: Sep. 28, 2000

(51) Int. Cl.[7] .................................................. A61F 2/00
(52) U.S. Cl. .......................................... 600/29; 128/885
(58) Field of Search ..................... 600/29–32; 128/885, 128/DIG. 25, 830–841; 604/11–18, 57, 59–60, 385.17, 904

(56) References Cited

U.S. PATENT DOCUMENTS

| | | |
|---|---|---|
| 2,355,628 A | 8/1944 | Calhoun |
| 2,739,593 A | 3/1956 | McLaughlin |
| 3,032,036 A | 5/1962 | Rader et al. |
| 3,409,011 A | 11/1968 | Mittag |
| 3,643,661 A * | 2/1972 | Crockford ................... 604/15 |
| 3,765,417 A | 10/1973 | Crockford |
| 3,918,452 A | 11/1975 | Cornfeld |
| 3,971,378 A * | 7/1976 | Krantz ................. 604/385.17 |
| 4,019,498 A * | 4/1977 | Hawtery et al. ............... 600/29 |
| 4,212,301 A * | 7/1980 | Johnson ................. 604/385.18 |
| 4,398,532 A | 8/1983 | Sweeney, III |
| 4,498,899 A | 2/1985 | Gross |
| 4,536,178 A | 8/1985 | Lichstein et al. |
| 4,573,963 A | 3/1986 | Sheldon |
| 4,573,964 A | 3/1986 | Huffman |
| 4,857,044 A | 8/1989 | Lennon |
| 4,921,474 A | 5/1990 | Suzuki et al. |
| 5,036,867 A * | 8/1991 | Biswas ..................... 600/30 X |
| 5,080,659 A | 1/1992 | Nakanishi |
| 5,395,308 A * | 3/1995 | Fox et al. ................ 604/904 X |
| 5,395,309 A | 3/1995 | Tanaka et al. |
| 5,554,109 A | 9/1996 | Frayman |
| 5,618,256 A * | 4/1997 | Reimer ......................... 600/29 |
| 5,659,934 A | 8/1997 | Jessup et al. |
| 5,755,906 A | 5/1998 | Achter et al. |
| 5,785,640 A * | 7/1998 | Kresch et al. ................. 600/29 |
| 5,795,346 A * | 8/1998 | Achter et al. ........... 604/904 X |
| 5,873,971 A * | 2/1999 | Balzar ..................... 604/904 X |
| 5,988,386 A | 11/1999 | Morrow |
| 6,019,743 A | 2/2000 | Cole et al. |
| 6,039,716 A | 3/2000 | Jessup et al. |
| 6,039,828 A | 3/2000 | Achter et al. |
| 6,056,714 A | 5/2000 | McNelis et al. |
| 6,071,259 A | 6/2000 | Steiger et al. |
| 6,090,038 A | 7/2000 | Zunker et al. |
| 6,090,098 A | 7/2000 | Zunker et al. |
| 6,095,998 A | 8/2000 | Osborn, III et al. |
| 6,142,928 A | 11/2000 | Zunker et al. |
| 6,248,089 B1 * | 6/2001 | Porat ............................ 604/17 |
| 6,270,470 B1 * | 8/2001 | Buck et al. ............. 604/904 X |

FOREIGN PATENT DOCUMENTS

| | | |
|---|---|---|
| DE | 1815375 | 9/1970 |
| GB | 1116742 | 6/1968 |

* cited by examiner

*Primary Examiner*—John P. Lacyk
(74) *Attorney, Agent, or Firm*—Brinks Hofer Gilson & Lione (57) ABSTRACT

Incontinence insert applicators for placing insert members within a vagina for reducing the occurrence and/or severity of female incontinence. The insert applicator has a non-circular cross-section for maximizing the available space for the insert, while also facilitating insertion of the applicator into the vagina. The applicators have orientation indicators to allow the user to properly orientate the inserts within the vagina.

17 Claims, 8 Drawing Sheets

INCONTINENCE INSERT APPLICATORS AND METHODS FOR THEIR USE

FIELD OF THE INVENTION

The present invention relates generally to devices for reducing the occurrence and/or severity of female urinary incontinence, and to methods for their use. In particular, the present invention relates to incontinence insert applicators for positioning and orientating an insert member within a vagina.

BACKGROUND

Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder and cause the involuntary release of urine. The frequency and severity of such urine loss can increase as the muscles and tissues near the urethro-vaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle can not close properly, therefore, the tendency for involuntary urine loss increases.

As the world's female population ages, there is an ever increasing need for a non-surgical procedure and/or device to reduce the involuntary urine loss commonly associated with "stress urinary incontinence." One way to alleviate the problem of incontinence is to place an insert within the vagina to press against and/or compress the urethra and provide support for the urethro-vaginal myofascial area in order to prevent the involuntary loss of urine. Inserts developed for such purposes are disclosed in U.S. Pat. Nos. 6,090,038 and 6,090,098; and in commonly assigned, co-pending U.S. application Ser. No. 09/217,395 entitled "A Urinary Incontinence Device and a Method of Making the Same," filed Dec. 21, 1998; U.S. application Ser. No. 09/675,459 entitled "A Urinary Incontinence Device and a Method of Making the Same," filed Sep. 28, 2000; and in U.S. application Ser. No. 09/675,460 entitled "Resilient Incontinence Insert and a Method of Making the Same," filed Sep. 28, 2000.

One challenge associated with the use of the inserts of the above mentioned patents and applications is that they should be properly oriented within the vagina in order to be most effective. Furthermore, because the inserts are relatively large compared to other vaginally inserted devices, such as catemenial tampons, there is a challenge making a device that can properly place the inserts within the vagina without causing discomfort. Accordingly, there continues to be a need for improvements in devices and methods for alleviating the problem of female urinary incontinence.

SUMMARY

In one aspect of the present invention, an insert member applicator includes an outer member adapted to house an insert member, and an inner member moveable within the outer member and operable to discharge the insert member from the outer member. At least the leading, vaginal insertion end portion of the outer member has a non-circular cross-section in a direction substantially perpendicular to the longitudinal axis of the outer member.

In another aspect of the invention, a device is provided for reducing the occurrence and/or severity of female urinary incontinence. The device includes an insert member and an applicator. The applicator includes an outer member adapted to house the insert, and an inner member moveable within the outer member and operable to discharge the insert member out of an exit portion of the outer member. The outer member is substantially cone-shaped and has its wider cross-section at the insert member exit portion, and the insert member is positioned within the outer member such that a portion of the insert member extends out of an exit portion of the outer member.

In another aspect of the invention, another device is provided for reducing the occurrence and/or severity of female urinary incontinence. The device includes an insert member and an applicator. The applicator includes an outer member adapted to house the insert member and an inner member moveable within said outer member and operable to discharge the insert member from an exit portion of the outer member. The outer member has a substantially elliptical cross-section in a direction substantially perpendicular to the longitudinal axis of the outer member.

Other aspects of the invention will be apparent to those of skill in the art in view of the appended claims.

DETAILED DESCRIPTION

Figure 1:
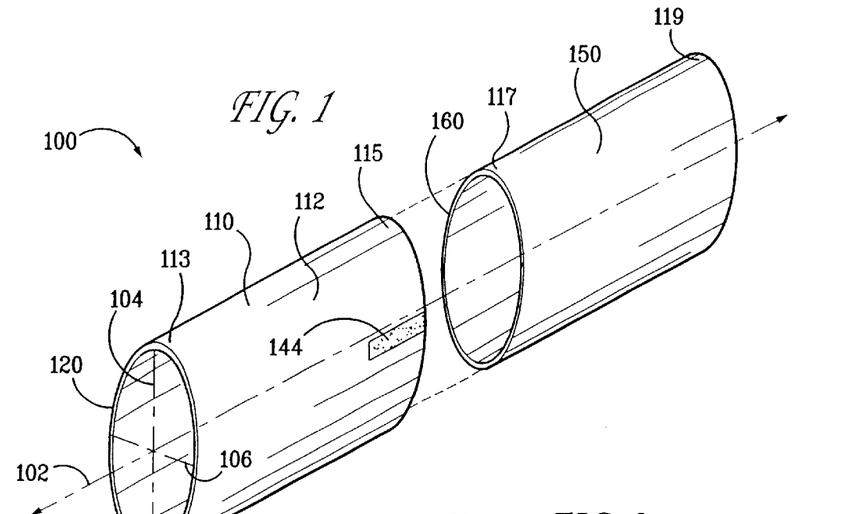
FIG. 1 is an exploded perspective view of a first embodiment of an insert applicator according to the present invention.

Referring now to the drawings and initially to FIG. 1, an insert member applicator according to the present invention is shown generally at 100 in a pre-assembled configuration. The applicator 100 has an outer member 110 defined by an insert carriage or insert housing, and an inner member 150 defined by a plunger or actuator. The outer member 110 is in the shape of a hollow cylinder 112 extending the entire longitudinal length of the outer member 110, that is, from a leading, vaginal insertion end portion 113 to a trailing end portion 115. The cylinder 112 extends substantially parallel to a longitudinal axis 102 of the applicator 100. In a direction substantially perpendicular to its longitudinal axis 102, the outer member 110 has a non-circular, substantially elliptical or oval cross-section having a major axis 104 defined by the longest diameter of the cross-section, and a minor axis 106 defined by the shortest diameter of the cross-section. The outer member 110 houses an insert member (not shown) that is to be discharged into the vaginal cavity.

The inner member 150 shares the common longitudinal axis 102 with the outer member 110, and extends from an insertion end portion 117 to a trailing end portion 119. The inner member 150 is sized and adapted to be moveable within the outer member 110, and is operable to discharge the insert member from an insert discharging exit end 120 of the outer member 110. The insert discharging exit end 120 is the leading end of the applicator 100 when the applicator is inserted into the vagina. Preferably, as shown, the inner member 150 also has a substantially oval or elliptical cross-section in a direction substantially perpendicular to its longitudinal axis 102. The cross-section of the outer member 110 is oval or elliptical (or substantially elliptical) rather than circular so as to more accurately approximate the shape of the vaginal opening, thereby facilitating the insertion of the applicator 100 into the vagina without discomfort to the user, while at the same time providing a volume that maximizes the space for housing an insert member.

The applicator 100 also preferably includes one or more orientation indicators. In the embodiment shown in FIG. 1, the orientation indicator is in the form of a marker 144, and is located on the outer surface of the outer member 110. The marker 144 is positioned so as to indicate the relative rotational position of the applicator 100, and hence, allows the user to correctly orient the insert member inside the vagina, as described more fully below. In the embodiment shown, the marker 144 is located on the minor axis of the elliptical cross-section of the outer member 110.

Figures 2, 3:
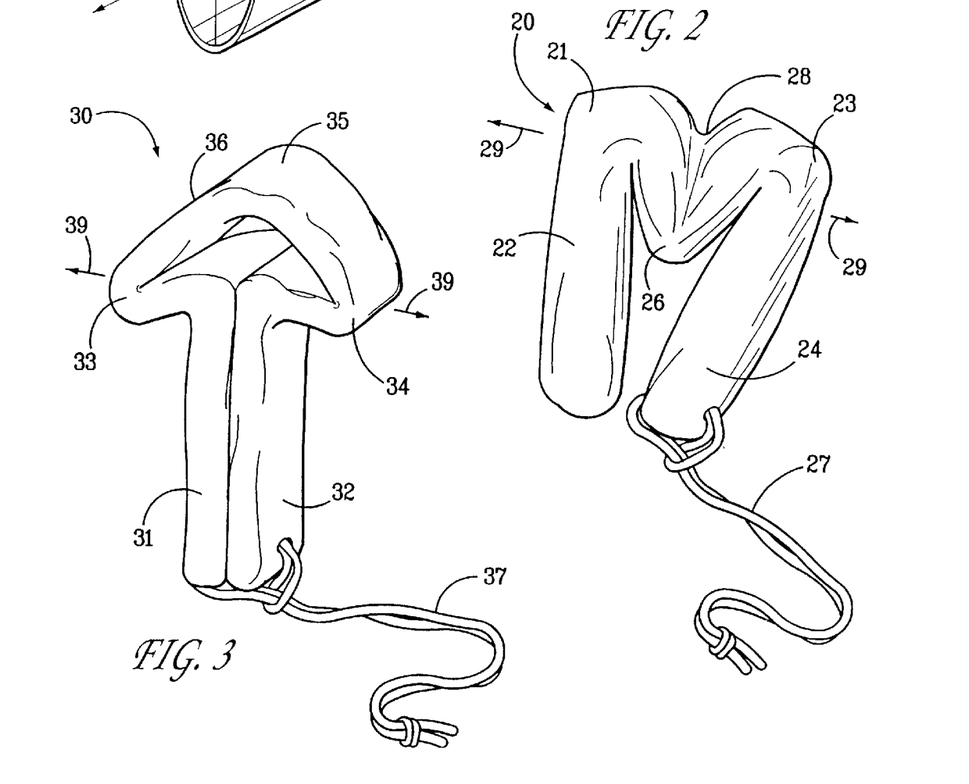
FIG. 2 is a perspective view of a first embodiment of an insert member for use with the applicators of the present invention.
FIG. 3 is a perspective view of a second embodiment of an insert member for use with the applicators of the present invention.

FIGS. 2 and 3 illustrate exemplary incontinence insert members according to the present invention. An "incontinence insert member" as used herein refers to devices specifically designed, configured, and/or adapted for placement into a vagina in order to reduce the occurrence and/or severity of female urinary incontinence. While incontinence insert members are typically made of non-absorbent materials, at least partially absorbent materials may also be used. However, there is no advantage to using absorbent materials because there is no intent to absorb any bodily fluids. Therefore, incontinence insert members are readily distinguishable from catamenial tampons.

In FIG. 2, an insert member having a "M-shape" profile in a plane parallel to the directions indicated by arrows 29, is shown generally at 20. Such inserts are more fully disclosed in commonly assigned co-pending U.S. application Ser. No. 09/217,395, entitled "A Urinary Incontinence Device and a Method of Making the Same," filed Dec. 21, 1998; U.S. application Ser. No. 09/675,459 entitled "A Urinary Incontinence Device and a Method of Making the Same," filed Sep. 28, 2000; and in U.S. application Ser. No. 09/675,460 entitled "Resilient Incontinence Insert and a Method of Making the Same," filed Sep. 28, 2000, all of which are hereby incorporated by reference in their entireties. Briefly, the insert 20 is formed from an elongated member having a first end portion 22 and a second end portion 24, and has three folds, 21, 23, and 26. The first end portion 22 and the second end portion 24 are aligned generally adjacent each other and, together with the folds 21, 23, 26, form a generally planar M-shaped profile. An inward crease 28 is formed in a direction generally perpendicular to the plane of the M-shaped profile. One of the end portions is attached to a withdrawal member, such as a string 27. The insert member 20 preferably includes, or is predominately made from, a resilient material that functions to expand the insert 20 in at least a direction indicated by arrows 29 once the insert 20 is placed within the vagina.

In order for the insert 20 to be most effective in reducing the occurrence and/or severity of incontinence, the insert 20 should be properly placed and correctly oriented within the vagina. Specifically, the insert 20 should expand in the direction 29 so as to press against and/or compress the urethra and support the urinary sphincter muscle, thereby reducing the occurrence and/or severity of incontinence, as more fully described in U.S. application Ser. No. 09/217,395. The applicators of the present invention help provide this correct orientation of the insert, as more fully described below with reference to FIGS. 8–10 and 15–17.

FIG. 3 illustrates an alternate embodiment of an insert useful for reducing the occurrence and/or severity of incontinence. Such inserts are more fully disclosed in U.S. Pat. Nos. 6,090,038 and 6,090,098, and in commonly assigned, co-pending U.S. application Ser. No. 09/675,460 entitled "Resilient Incontinence Insert and a Method of Making the Same," filed Sep. 28, 2000, all of which are incorporated herein by reference in their entireties. Briefly, the insert 30 is formed from an elongated member that includes a first end portion 31 and a second end portion 32, and a connecting portion 36. The first end portion 31 and the second end portion 32 are aligned adjacent each other, and the connecting portion 36 includes three folds 33, 34, 35 in order to form a generally planar closed loop dome-shaped profile. The dome-shaped profile is in a plane parallel to the direction indicated by arrows 39. In this embodiment, both end portions are attached to a withdrawal member, such as a string 37. The insert 30 preferably includes, or is predominately made from, a resilient material that functions to expand the insert 30 in at least a direction indicated by arrows 39 once the insert 30 is placed within the vagina. Like the insert of FIG. 2, the insert 30 should be properly placed and oriented within the vagina to maximize its effectiveness. The insert 30 must expand in the direction 39 so as to press against and/or compress the urethra and support the urinary sphincter muscle, thereby reducing the occurrence and/or severity of incontinence, as more fully described in U.S. Pat. Nos. 6,090,038 and 6,090,098. The applicators of the present invention help provide this correct orientation of the insert, as more fully described below with reference to FIGS. 8–10 and 15–17.

Figure 4:
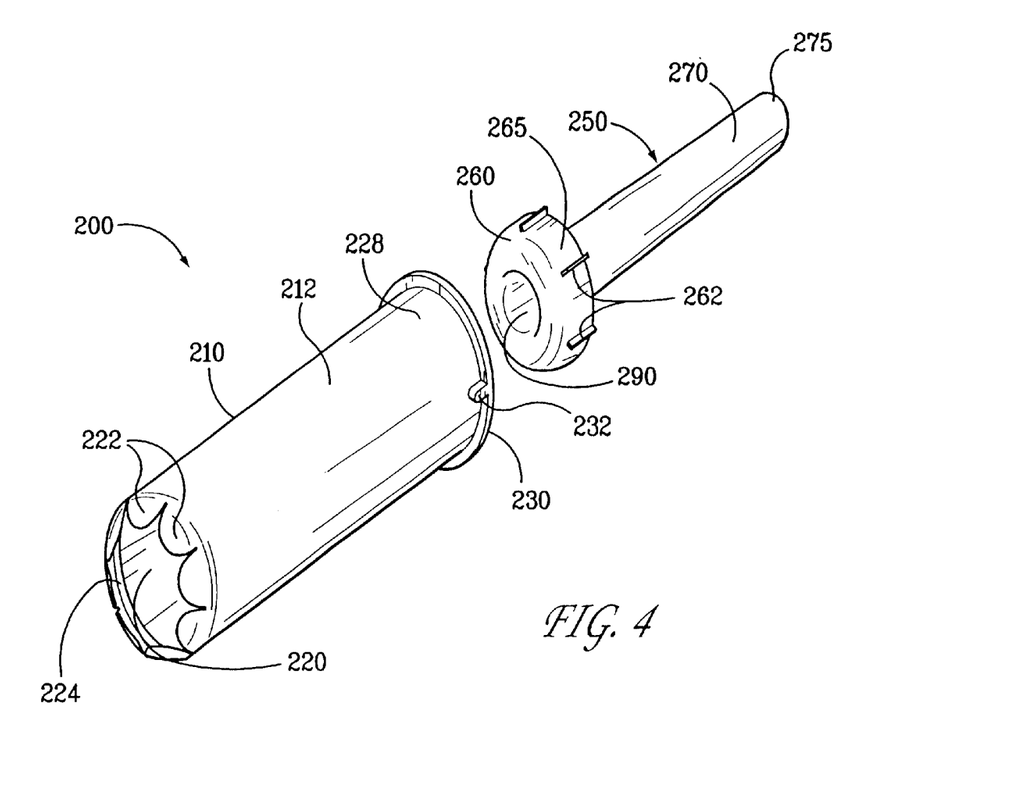
FIGS. 4 and 5 are exploded perspective views of a second embodiment of an insert applicator according to the present invention.
Figure 5:
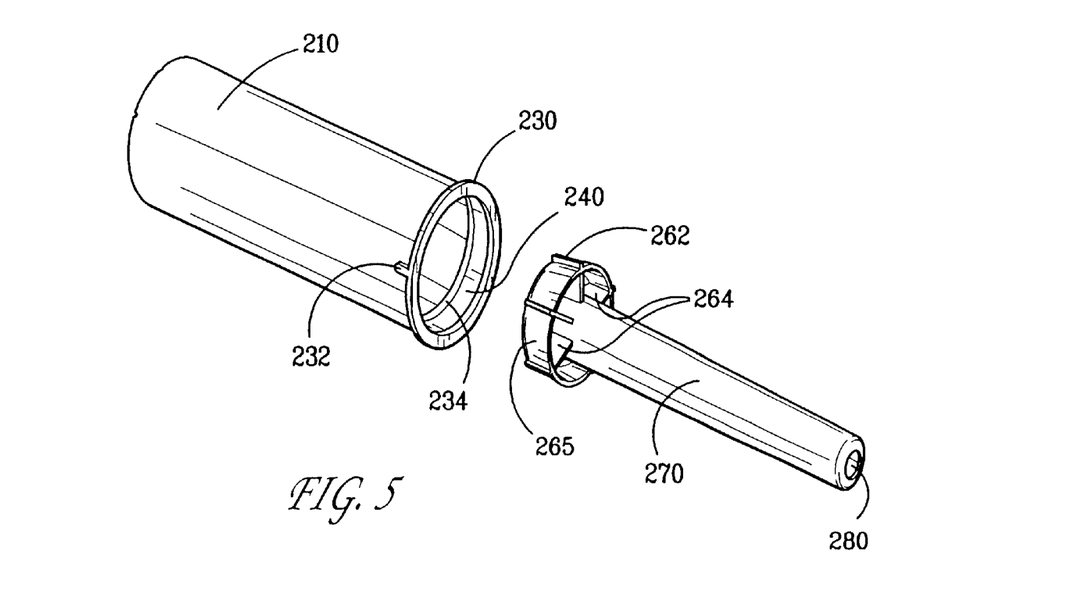
Figure 7:
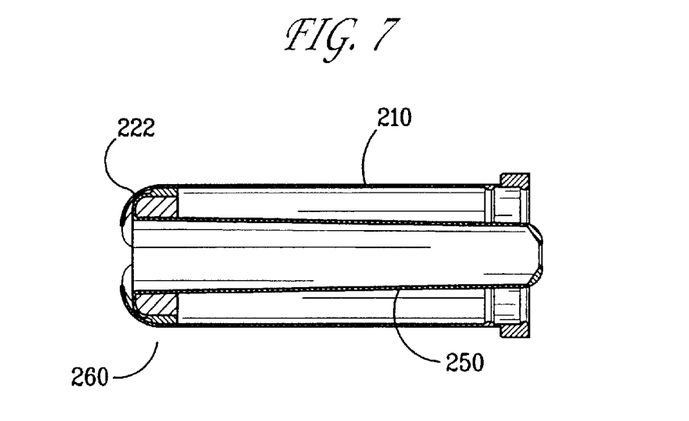
FIG. 7 is a longitudinal cross-sectional view of the insert applicator of FIGS. 4 and 5 in an insert discharging position.

Turning now to FIGS. 4–5, an alternate embodiment of the insert applicator according to the present invention is shown generally at 200 in a pre-assembled configuration. The applicator 200 includes an outer member 210 defining an insert carriage or insert housing, and an inner member 250 for discharging an insert from the outer member 210. The outer member 210 includes a hollow cylinder 212 extending substantially parallel to a longitudinal axis (not shown). In a direction substantially perpendicular to its longitudinal axis, the outer member 210 has a substantially oval or elliptical cross-section. The outer member 210 has an insert discharging exit end 220 and a trailing end 240. The insert discharging exit end 220 is the leading, vaginal insertion end when the applicator 200 is inserted into the vagina. The exit end portion of the cylinder 212 preferably includes flanges defining petals 222, which soften the vaginal insertion process, and a retaining rib 224 for providing a tactile stop for the inner member as shown in FIG. 7. However, in alternate embodiments, the exit end portion may be petal-less. The trailing portion of the cylinder 212 has a gripping portion 228 including a raised edge 230, and orientation indicators 232 defined by a pair of orientations tabs. The orientation indicators are located on the outer surface of the outer member 210 near or adjacent the gripping portion 228, and indicate to the user the location of the minor axis of the elliptical cross-sectioned outer member 210.

The inner member 250 of the applicator 200 includes a head portion 260, a shank portion 270 and a trailing portion 275. Like the outer member 210, the inner member 250 preferably has a substantially elliptical cross-section in a direction perpendicular to its longitudinal axis. The inner member 250 is hollow, and has exits 280, 290 for threading an insert withdrawing member, such as a string, through the interior of the inner member 250 and out the rear of the applicator 200. The head portion 260 is integrally formed with the shank portion 270 by a continuous return flange 265 extending from the exit 290 back towards the trailing portion 275. The flange 265 is preferably reinforced by support members 264 connected with the outer surface of the shank portion 270. The flange 265 includes a plurality of outer member engaging portions defined by extensions 262 for contacting the interior of the outer member 210. Although the flange 265 shown extends a relatively short length relative to the full length of the inner member 250, in other embodiments, the flange 265 extends significantly longer relative to the length of the inner member 250.

Figure 6:
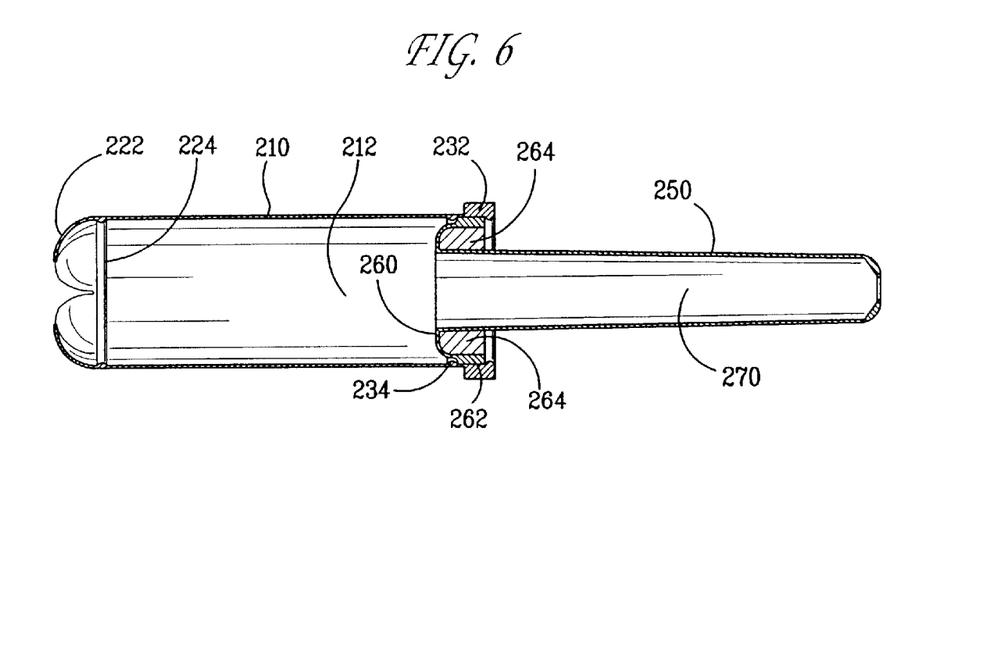
FIG. 6 is a longitudinal cross-sectional view of the insert applicator of FIGS. 4 and 5 in an insert housing position.

FIGS. 6 and 7 illustrate the applicator 200 in an assembled configuration. FIG. 6 illustrates the applicator 200 in its insert housing position (insert not shown), whereas FIG. 7 illustrates the applicator in its insert discharging position. As shown in FIG. 6, the head portion 260 rests in the trailing end 240 of the outer member 210 with the extensions 262 slideably engaging the inner surface of the outer member 210. In alternate embodiments, the head portion 260 may rest at a location more advanced into the outer member 210. The head portion 260 is held in place longitudinally by a retaining rib 234. The applicator 200 is formed of a material, such as a thermoplastic, that allows for slight deformation of the extensions 262 when the inner member 250 is pushed by the user, thereby allowing the extensions 262 to pass the retaining rib 234, and to allow the inner member 250 to advance through the interior of the outer member 210.

The shank portion 270 has a substantially smaller cross-section than the head portion 260. Because of this smaller cross-section, the user is able to actuate the inner member 250 with a single finger of the user's same hand that is holding the outer member 210 at the gripping portion 228. Furthermore, the smaller cross-section shank portion 270 is more aesthetically pleasing because it makes the applicator as a whole appear smaller and less likely to cause discomfort in its use.

Figures 8, 9, 10:
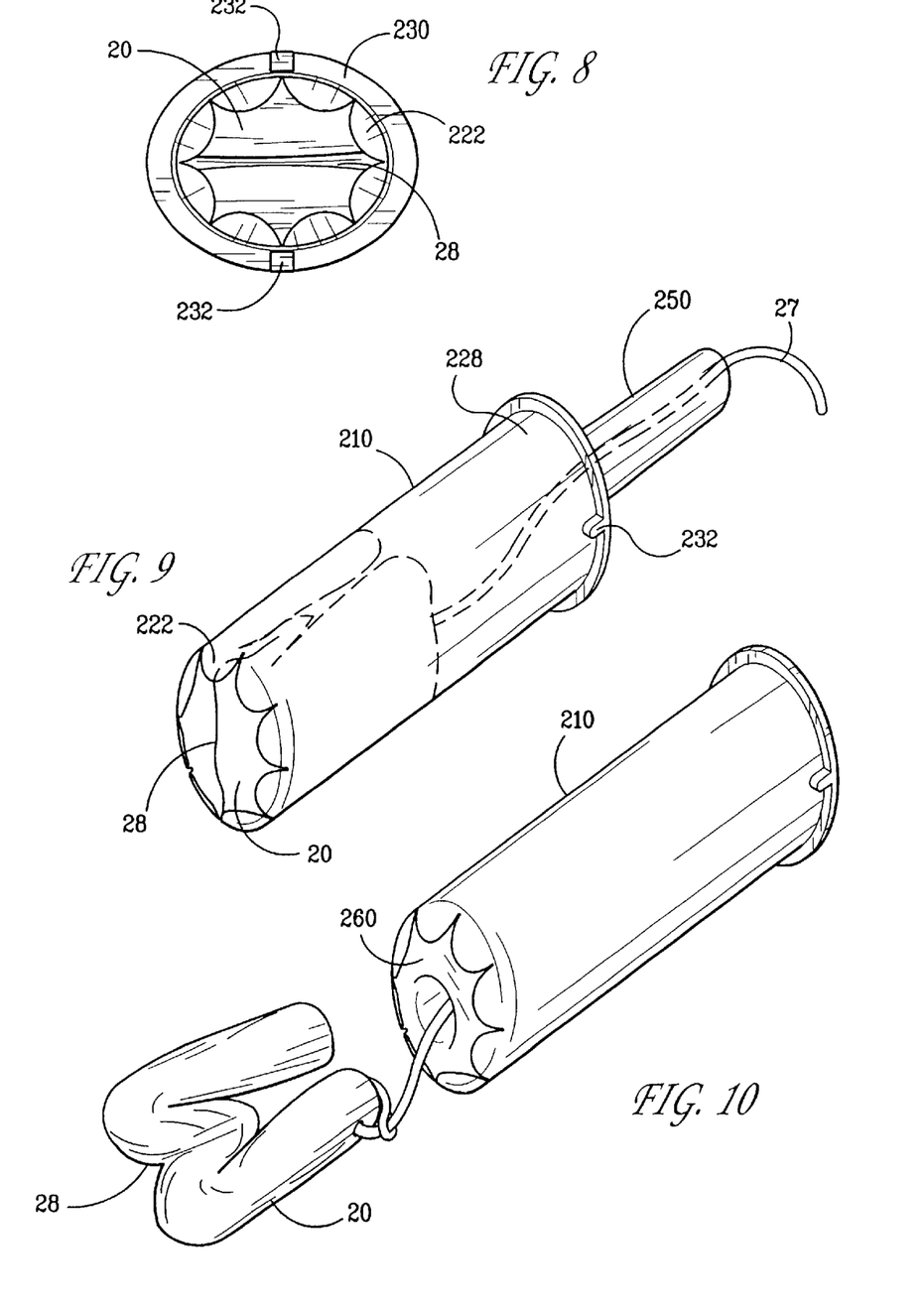
FIG. 8 is a front view of the second embodiment of the insert applicator according to the present invention, housing the insert of FIG. 2.
FIG. 9 is a perspective view of the second embodiment of the insert applicator in the insert housing position, and also shows the insert member of FIG. 2 in phantom.
FIG. 10 is a perspective view of the second embodiment of the insert applicator in the insert discharging position, and also shows the insert member of FIG. 2 discharged from the insert applicator.

FIGS. 8 to 10 illustrate the use of the applicator 200 with the insert 20 of FIG. 2. FIG. 8 illustrates a front cross-sectional view of the applicator 200, shown housing the insert 20. FIG. 9 illustrates the insert 20 in phantom within the outer member 210, and FIG. 10 illustrates the insert discharged from the outer member 210. As shown, the inward crease 28 of the insert 20 is substantially parallel to the major axis of the elliptical cross-section, and substantially perpendicular to the minor axis of the elliptical cross-section and an imaginary line connecting the orientation indicators 232. The insert 20 is therefore oriented within the outer member 210 such that the plane defined by the M-shaped profile of the insert 20 is substantially parallel to the minor axis of the substantially elliptical cross-section.

To correctly orient the insert 20, the user simply discharges the insert in a position so that it expands in a direction indicated by arrow 29 (FIG. 2) towards the urethra and provides support to the urinary sphincter muscle.

This can be accomplished simply by discharging the insert 20 only when the applicator 200, having been inserted into the vagina, is oriented such that an imaginary line connecting the two orientation indicators 232 are substantially parallel with the major axis of the opening of the vagina. As used herein, the major axis of the opening of the vagina is defined as the axis across the opening of the vagina generally extending in direction from the prepuce of the clitoris to the fourchet and/or the anal opening.

Those skilled in the art will recognize that the applicator 200 is also useful with the insert 30 shown in FIG. 3, as well other inserts. Those skilled in the art will appreciate that various modifications may be made to the incontinence insert members shown. For example, the manners of attachment of the withdrawing member shown in FIGS. 2 and 3 are only exemplary, and other manners known in the art can be used equally as well. However, while various modifications may be made to the inserts shown, the advantages of the applicator 200 are most apparent and fully realized where the effective functioning of the insert is at least in part dependent upon its correct orientation within the vagina, as is the, case for the inserts of FIG. 2 and FIG. 3.

Figure 11:
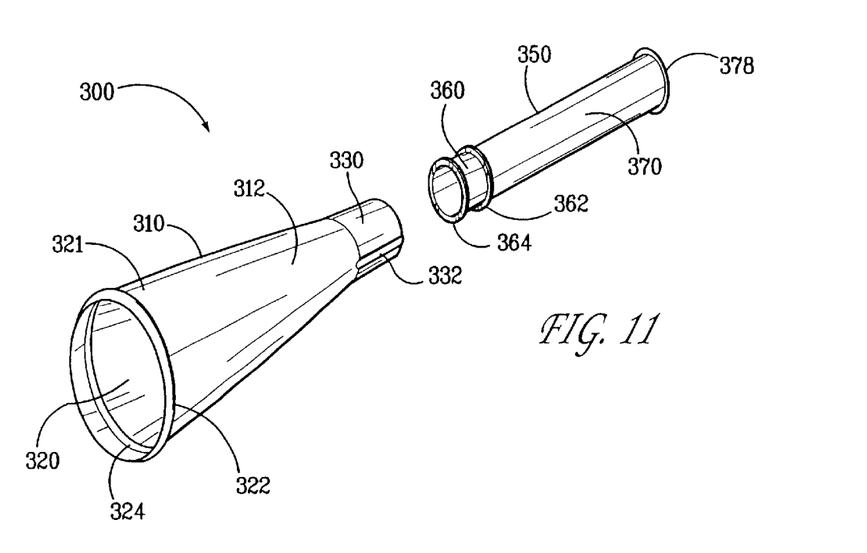
FIGS. 11 and 12 are exploded perspective views of a third embodiment of an insert applicator according to the present invention.
Figure 12:
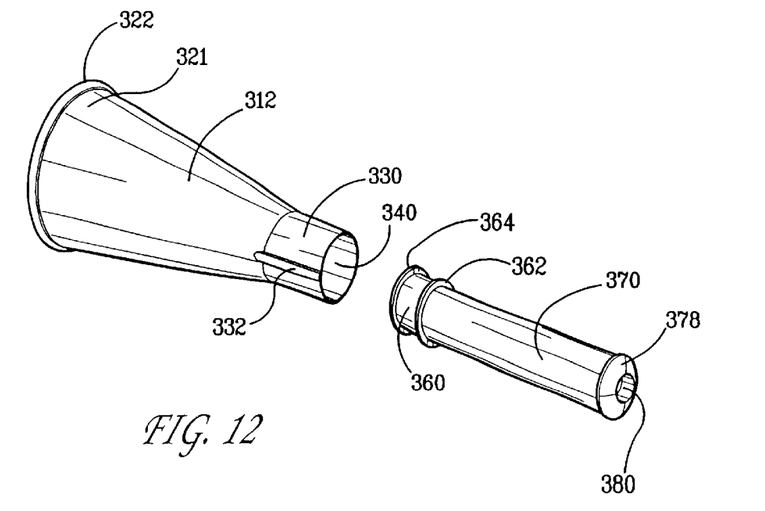

Turning now to FIGS. 11–12, another alternate embodiment of the insert applicator is shown generally at 300 in a pre-assembled configuration. The applicator 300 includes an outer member 310 defining an insert carriage or insert housing, and an inner member 350 for discharging an insert member from the outer member 310. The outer member 310 includes a substantially cone-shaped portion 312, and a substantially cylindrical-shaped portion 330 extending substantially parallel to a longitudinal axis (not shown). In a direction substantially parallel to its longitudinal axis, the coned-shaped portion 312 and the cylindrical portion 330 both have a substantially oval or elliptical cross-section. The outer member 310 also has an insert discharging exit end 320 and a trailing end 340. The insert discharging end 320 is the leading, vaginal insertion end when the applicator 300 is inserted into the vagina. The cone-shaped portion 312 has a wider cross-section at the exit end 320, and a smaller cross-section connected with the cylindrical portion 330. The vaginal insertion end portion 321 of the outer member 310 is this embodiment has a raised edge 322 with a continuous surface, that is, the vaginal insertion end portion 321 has no flanges and is petal-less. The vaginal insertion end portion 321 also includes a retaining rib 324 for steadying the incontinence insert in place before it is discharged by the inner member 310. The cylindrical portion 330 defines a gripping portion for the outer member, and also includes orientation indicators 332 defined by a pair of orientation tabs. The orientation indicators 332 are located on the outer surface of the outer member 310 and indicate the location of the minor axis of the elliptical cross-sectioned outer member 310.

The inner member 350 of the applicator 300 includes a head portion 360 and a shank portion 370. Like the outer member 310, the inner member 350 preferably has an elliptical cross-section in a direction substantially perpendicular to its longitudinal axis. The inner member 350 is hollow, and has exits 380, 390 for threading an insert withdrawing member, such as a string, through the interior of the inner member 350 and out the rear of the applicator 300. The head portion 360 is integrally formed with the shank portion 370 and includes retaining ribs 362 and 364.

The shank portion 370 has a substantially smaller cross-section than the outer member 310. Because of this smaller cross-section, the user is able to actuate the inner member 350 with a single finger of the user's same hand that is holding the outer member 310 at the cylindrical portion 330. Furthermore, the smaller cross-section shank portion 370 is more aesthetically pleasing because it makes the applicator as a whole appear smaller and less likely to cause discomfort in its use.

Figure 13:
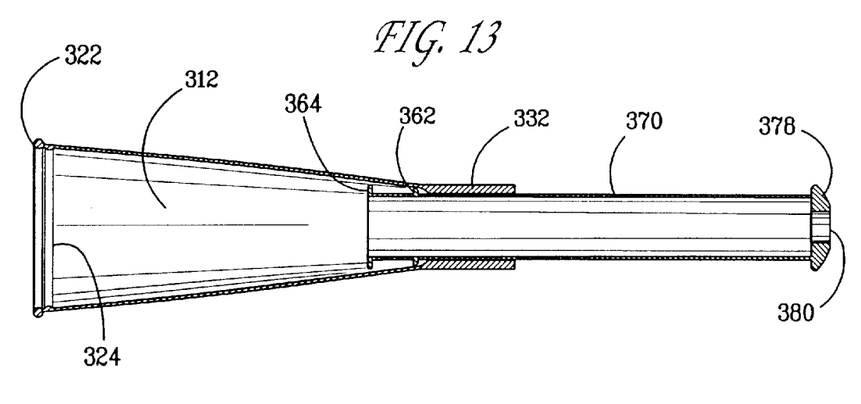
FIG. 13 is a longitudinal cross-sectional view of the insert applicator of FIGS. 11 and 12 in an insert housing position.
Figure 14:
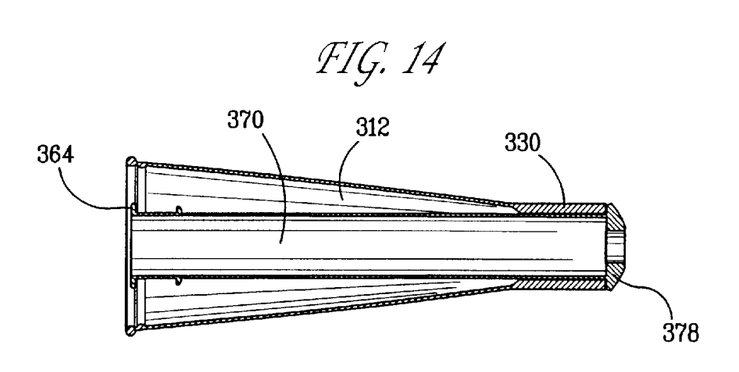
FIG. 14 is a longitudinal cross-sectional view of the insert applicator of FIGS. 11 and 12 in an insert discharging position.

FIGS. 13 and 14 illustrate the applicator 300 in an assembled configuration. FIG. 13 illustrates the applicator 300 in its insert housing position (insert not shown), whereas FIG. 14 illustrates the applicator in its insert discharging position. As shown in FIG. 13, the head portion 360 rests in a trailing end 340 of the outer member 310, and the retaining rib 362 prevents the head portion 360 from entering the cylindrical portion 330 and thereby preventing the inner member 350 from being removed from the outer member 310. The inner member 350 also includes a tail portion 378. As shown, the tail portion 378 is preferably rounded to facilitate forcible insertion of the inner member 350 through the insert discharging exit end 320 and then through the cylindrical portion 330 during assembly of the applicator. The applicator 300 is formed of a material, such as a thermoplastic, that allows for slight deformation of the tail portion 378 when inner member 350 is pushed through during assembly. Once assembled, the retaining rib 362 and the tail portion 378 prevent the inner member 350 from being fully removed from the outer member 310.

Figure 15:
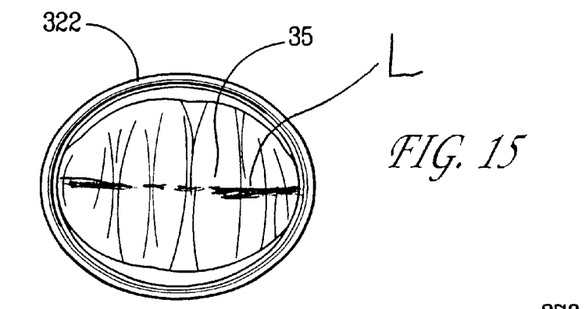
FIG. 15 is a front view of the third embodiment of the insert applicator according to the present invention, housing the insert of FIG. 3.
Figures 16, 17:
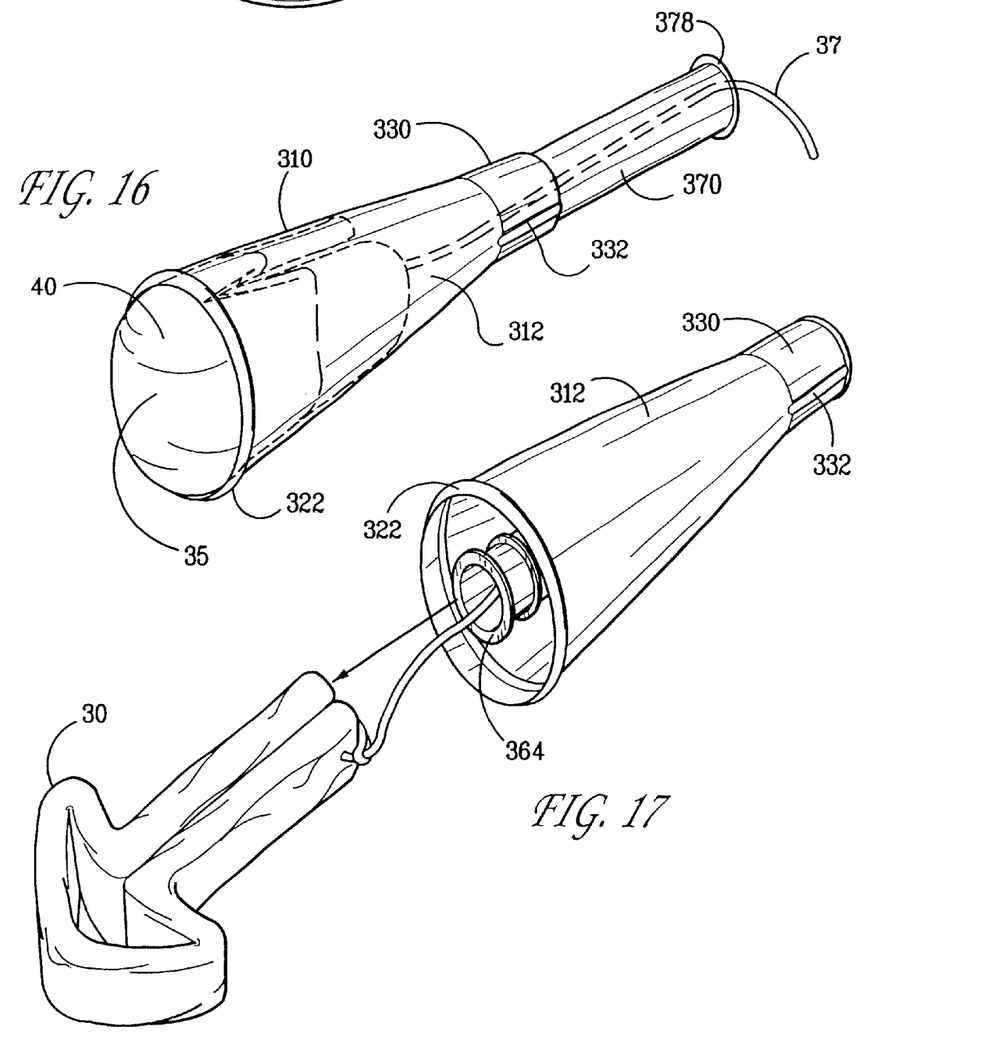
FIG. 16 is a perspective view of the third embodiment of the insert applicator in the insert housing position, and also shows the insert member of FIG. 3 in phantom.
FIG. 17 is a perspective view of the third embodiment of the insert applicator in the insert discharging position, and also shows the insert member of FIG. 3 discharged from the insert applicator.

FIGS. 15 to 17 illustrate the use of the applicator 300 with the insert 30 of FIG. 3. FIG. 15 illustrates a front cross-sectional view of the applicator 300, shown housing the insert 30. FIG. 16 illustrates the insert 30 in phantom within the outer member 310, and FIG. 17 illustrates the insert discharged from the outer member 310. As shown in FIG. 15, a length L of the top fold 35 transverse to the plane formed by the dome-shaped profile of the insert 30 is substantially parallel to the major axis of the elliptical cross-section, and substantially perpendicular to the minor axis of the substantially elliptical cross-section and an imaginary line connecting the orientation indicators 332. The insert 30 is therefore oriented within the outer member 310 such that the plane defined by the dome-shaped loop profile of the insert 30 is substantially parallel to the minor axis of the elliptical cross-section. Furthermore, as best seen in FIG. 16, a top portion 40 of the insert 30 extends out of the insert discharging exit end 320 of the outer member 310 when the applicator 300 is in its insert housing position. This positioning of the insert 30 allows for ease of insertion of the petal-less applicator into the vagina.

To correctly orient the insert 30, the user must simply discharge the insert in a position so that it expands in a direction by the arrows 39 (FIG. 2) towards the urethra. This can be accomplished simply by discharging the insert 30 only when the applicator 300, having been inserted into the vagina, is oriented such the orientation indicators 332 are substantially parallel with the major axis of the opening of the vagina.

Those skilled in the art will recognize that the applicator 300 is also useful with the insert 20 shown in FIG. 2, as well other incontinence inserts.

However, the advantages of the applicator 300 are most apparent and fully realized where the effective functioning of the insert is at least in part dependent on correct orientation within a vagina, as is the case for the inserts of FIG. 2 and FIG. 3.

The applicators of the present invention should be made of a biocompatible material, such as a paperboard stock, or a plastic. The outer member 110 is preferably about 50 to 75 mm in length, more preferably about 60 to 70 mm, and most preferably about 65 mm. The major axis of the elliptical cross-section is preferably about 20 to 40 mm in length, more preferably about 25 to 35 mm, and most preferably about 30 mm. The minor axis of the elliptical cross-section is about 10 to 30 mm in length, more preferably about 10 to 20 mm, and most preferably about 15 mm. The inner member 150 is preferably about 50 mm to about 100 mm in length, more preferably about 65 to 85 mm, and most preferably about 75 mm.

Various modifications may be made to the applicators shown without departing from the scope of the present invention. For example, the cylindrical portion 330 of the applicator 300 may include a raised edge similar to the raised edge 230. In addition, while it is preferred that the orientation indicators are located on the minor axis of the elliptical cross-section of the outer member, the orientation indicators may alternately be placed on other areas of the outer members, as well as on the inner member. The orientation indicators may also be significantly larger than those shown. In addition, while the orientation indicators have been shown as marks or tabs, the orientation indicators may be formed of other structures, such as indicia.

Furthermore, although the applicators shown have a substantially elliptical cross-section for the entire longitudinal length of both the outer member and the inner member, some applicators within the scope of the invention may have a substantially elliptical cross-section for less than the entire longitudinal length of either the outer member and/or the inner member. In the preferred embodiments, the applicators will have a substantially elliptical cross-section at least at the leading, vaginal insertion end portion of the outer member, with the option of having a more conventional or circular cross-section the rest of the length. In more preferred embodiments, the applicators will have a substantially elliptical cross-section for a substantial portion of the longitudinal length of the outer member and/or inner member. In even more preferred embodiments, the applicators will have a substantially elliptical cross-section for at least half the longitudinal length, and in even more preferred embodiments, the substantially elliptical cross-section will extend at least three-quarters the longitudinal length of the outer member and/or inner member. In the most preferred embodiment, the applicators will have a substantially elliptical cross-section for substantially the entire length of the outer member and/or inner member.

FIGS. 18A–18D illustrate cross-sections of alternate embodiments of the applicators of the present invention. As previously mentioned, the most preferred applicators have substantially elliptical cross-sections in at least in their leading, vaginal insertion end portions, in order to accurately approximate the shape of the opening of the vagina, thereby facilitating the insertion of the applicator, while also maximizing the space available for housing an insert member. However, other cross-sections, while perhaps not facilitating the insertion process as well as a substantially elliptical cross-section, are advantageous nevertheless to maximize the space for housing a particular insert, such as an insert member having an asymmetrical shape.

Figure 18A:
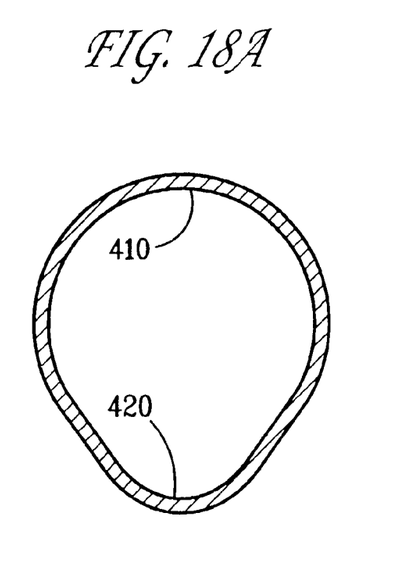
FIGS. 18A–18D are cross-sectional views of alternate embodiments of the applicator according to the present invention.

FIG. 18A illustrates an alternate embodiment of the applicators having non-circular cross-section according to the present invention. The cross-section is substantially "egg-shaped," that is, one portion 410 of the cross-section is substantially circular in contour, and another portion 420, continuous with the substantially circular portion 410, is substantially elliptical in contour.

Figure 18B:
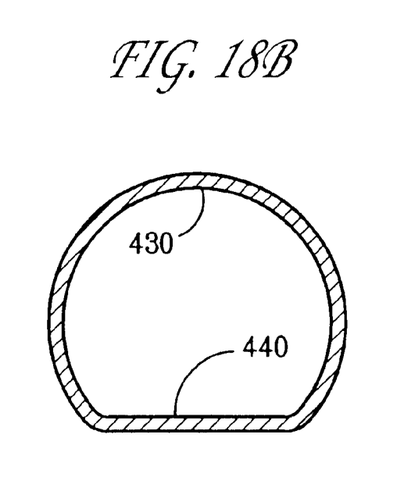

FIG. 18B illustrates another alternate cross-section for the applicators of the present invention. The cross-section includes one portion 430 that is substantially circular in contour, and another portion 440, continuous with the substantially circular portion 430, is substantially flat or straight.

Figure 18C:
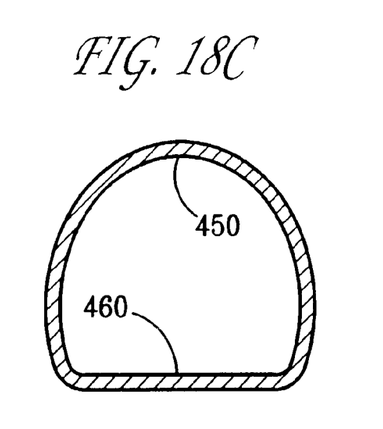

FIG. 18C illustrates a third alternate cross-section for the applicators of the present invention. The cross-section includes one portion 450 that is substantially elliptical in contour, and another portion 460, continuous with the substantially elliptical portion 450, is substantially flat or straight.

Figure 18D:
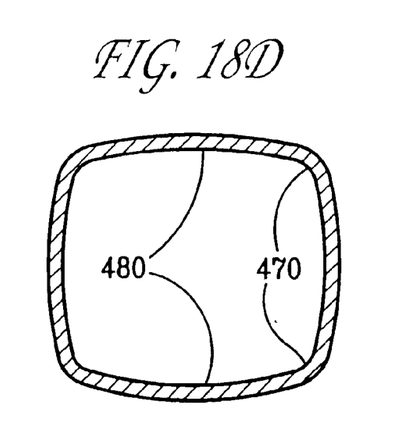

FIG. 18D illustrates a fourth alternate cross-section for the applicators of the present invention. The cross-section is defined herein as a "soft-square," that is, the cross-section is substantially a square, however its corners 470 and/or the sides 480 are slightly or softly curved. Other slightly curved quadrilaterals may also be used may for the cross-sections, such as soft-rectangles and soft-trapezoids.

Like the substantially elliptical cross-sections, the alternate cross-sections of FIGS. 18A–18D are shown in a direction substantially perpendicular to the longitudinal axis of the applicator. Furthermore, the alternate non-circular cross-sections of FIGS. 18A–18D need not extend the entire length of the applicator, but rather may be combined with other cross-sections. The preferred alternate embodiments of the applicators will have the cross-sections of any of FIGS. 18A–18D at least at the leading, vaginal insertion end portion of the outer member. In more preferred embodiments, the applicators will have one of the alternate cross-sections for a substantial portion of the longitudinal length of the outer member and/or inner member. In even more preferred embodiments, the applicators will have an alternate cross-section for at least half the longitudinal length, and in even more preferred embodiments, the alternate cross-section will extend at least three-quarters the longitudinal length of the outer member and/or inner member. In the most preferred embodiment, the applicators will have an alternate cross-section for substantially the entire length of the outer member and/or inner member.

According to another aspect of the present invention, a method is provided for properly positioning an insert member within a vagina so that the insert member is effective in reducing the occurrence and/or severity of involuntary urine loss. The method uses an insert applicator according to the present invention. Specifically, the preferred applicators useful in the method have a non-circular cross section, such as an elliptical cross-section, or one of the cross-sections shown in FIGS. 18A–18D.

In one embodiment of the method, the applicator is inserted into the vagina such that the major axis of the substantially elliptical cross-section of the applicator is substantially parallel with the major axis of the opening of the vagina. The applicator is inserted and advanced into the vagina until either the fingers of the user that are holding the gripping portion of the applicator are resting against the body, or until the gripping portion is flush with the vaginal opening. Typically, the applicator is advanced approximately 2 to 3 inches. After inserting the applicator, the applicator is rotated about 90 degrees such that the minor axis of the elliptical cross-section is substantially parallel with the major axis of the opening of the vagina. The insert is then discharged into the vagina in its proper orientation.

In an alternate embodiment, where the applicators have orientation indicators, the applicator is oriented based upon the orientation indicators. Preferably, the applicator is first inserted into the vagina, and then oriented by rotation based upon the orientation indicators. Alternately, the applicator may be oriented before insertion based upon the orientation indicators, so that the applicator is correctly oriented when inserted. The insert is then discharged into the vagina in its correct orientation.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A device for reducing the occurrence and/or severity of female incontinence, comprising:
    an incontinence insert member;
    an applicator comprising an outer member and an inner member; said outer member adapted to house said insert member; said inner member moveable within said outer member and operable to discharge said insert member out of an insert discharging exit end of said outer member; said outer member substantially cone-shaped with its wider cross-section at said exit end;
    said outer member being elliptically shaped, and forming an orientation means for orienting said device within the opening of a vagina;
    said insert member positioned within said outer member such that a portion of said insert member extends out of said exit end.

2. The device of claim 1, wherein said insert member comprises an elongated member having a first end portion, a second end portion, and a connecting portion between said first end portion and said second end portion, said elongated member being folded upon itself such that said first and second end portions are aligned and adjacent to one another forming a generally dome-shaped loop.

3. The device of claim 1, wherein said applicator further comprises at least one orientation indicating tab indicating the minor axis of said elliptical cross-section.

4. A device for reducing the occurrence and/or severity of female incontinence, comprising:

an incontinence insert member;

an applicator comprising an outer member and an inner member; said outer member adapted to house said insert member and said inner member moveable within said outer member and operable to discharge said insert member from an exit portion of said outer member; wherein at least said exit portion of said outer member has a substantially elliptical cross-section in a direction substantially perpendicular to the longitudinal axis of said outer member; and wherein said substantially elliptical cross-section forms an orientation means for orienting said device within the opening of a vagina.

5. The device of claim 4, wherein said inner member comprises a head portion and a shank portion, said head portion adapted to slideably engage the inner surface of said outer member.

6. The device of claim 4, wherein said insert member comprises an elongated member having a first end portion and a second end portion, said elongated member being folded upon itself such that said first and second end portions are aligned adjacent to one another and said elongated member contains at least three folds therebetween to form a generally M-shaped profile.

7. The device of claim 6, wherein said first end portion, said second end portion, and said folds together generally define a plane, said elongated member positioned such that said plane is substantially parallel to the minor axis of said substantially elliptical cross-section.

8. A method for positioning an incontinence insert member within a vagina, comprising:

inserting an applicator into a vagina, said applicator comprising an outer member, an inner member, an incontinence insert member, and at least one orientation indicator; said outer member housing said insert member, said inner member operable to discharge said insert member from said outer member, and said at least one orientation indicator positioned on an outer surface of said applicator;

orientating said applicator based upon the position of said at least one orientation indicator; and discharging said insert member into the vagina.

9. The method of claim 8, wherein said orientating of said applicator occurs after said inserting of said applicator.

10. The method of claim 8, wherein said outer member comprises an elliptical cross-section in a direction substantially perpendicular to the longitudinal axis of said outer member.

11. The method of claim 10, wherein said at least on orientation indicator is located on said outer member at a position indicating the minor axis of said outer member.

12. The method of claim 8, wherein said insert member is adapted to reduce the occurrence and/or severity of female incontinence.

13. A method for positioning an insert member within a vagina, comprising:

inserting an applicator into a vagina, said applicator comprising an outer member, an inner member, and an insert member; said outer member housing said insert member and having an elliptical cross-section in a direction substantially perpendicular to the longitudinal axis of said outer member; said inner member operable to discharge said insert member from said outer member; said applicator inserted such that the major axis of said elliptical cross-section is substantially parallel with the major axis of the opening of the vagina;

orientating said applicator by rotating the applicator about 90 degrees such that the minor axis of said elliptical cross-section is substantially parallel with the major axis of the opening of the vagina;

discharging said insert member into the vagina.

14. The method of claim 13, wherein said applicator further comprises at least one orientation indicator representing the minor axis of said elliptical cross-section.

15. The method of claim 13, wherein said insert member is adapted to reduce the occurrence and/or severity of female incontinence.

16. The method of claim 13, wherein said insert member comprises an elongated member having a first end portion, a second end portion, and a connecting portion between said first end portion and said second end portion, said member being folded upon itself such that said first and second end portions are aligned adjacent to one another forming a generally dome-shaped loop; and wherein said insert member expands upon discharge.

17. The method of claim 13, wherein said insert member comprises an elongated member having a first end portion and a second end portion, said elongated member being folded upon itself such that said first and second portions are aligned adjacent to one another and said member contains at least three folds therebetween to form a generally M-shaped profile; and wherein said insert member expands upon discharge.

* * * * *